United States Patent [19]
Scheib et al.

[11] Patent Number: 5,682,896
[45] Date of Patent: Nov. 4, 1997

[54] METHOD AND APPARATUS FOR GENERATING VOLUME FLOW MEASUREMENT

[75] Inventors: John P. Scheib, Santa Clara, Calif.; Cindy A. Owen, Memphis, Tenn.

[73] Assignee: Diasonics Ultrasound, Inc., Santa Clara, Calif.

[21] Appl. No.: 624,192

[22] Filed: Mar. 28, 1996

[51] Int. Cl.$^6$ .................................................. A61B 8/00
[52] U.S. Cl. ........................................................ 128/661.1
[58] Field of Search ..................... 128/661.08, 661.09, 128/661.1, 660.05; 73/861.25

[56] References Cited

U.S. PATENT DOCUMENTS 4,630,612  12/1986  Uchida et al. .................. 128/661.09
4,873,985  10/1989  Nakajima ........................ 128/661.09

*Primary Examiner*—George Manuel
*Attorney, Agent, or Firm*—Blakely, Sokoloff, Taylor & Zafman LLP

[57] ABSTRACT

A computer implemented method and apparatus for generating a vascular volume flow measurement in a living subject using an ultrasonic system by determining a velocity measurement and an area measurement at the same location in a blood vessel. The present invention generates an angle correct cursor on a display indicating where in a vessel a velocity measurement is being obtained. A diameter measure cursor is fixed perpendicular to the angle correct cursor to determine a diameter of the vessel at the same location of the vessel where the velocity measurement is obtained. The diameter is multiplied with the time averaged means velocity to accurately generate the volume flow. In one embodiment, the length of the diameter measure cursor is adjustable to extend a first end and an opposing second end of the diameter measure cursor, approximately to the walls of the vessel. In a second embodiment, the diameter measure cursor is adjustable to slide the cursor along its length to be approximately in a center of the vessel, while maintaining the diameter measure cursor to be perpendicular to the angle correct cursor. The velocity measurement, in the present invention, is generated by emitting pulses into a subject under examination, receiving echoes and determining Doppler frequency shifts from the pulses, and translating the Doppler frequency shifts to velocity information.

25 Claims, 4 Drawing Sheets

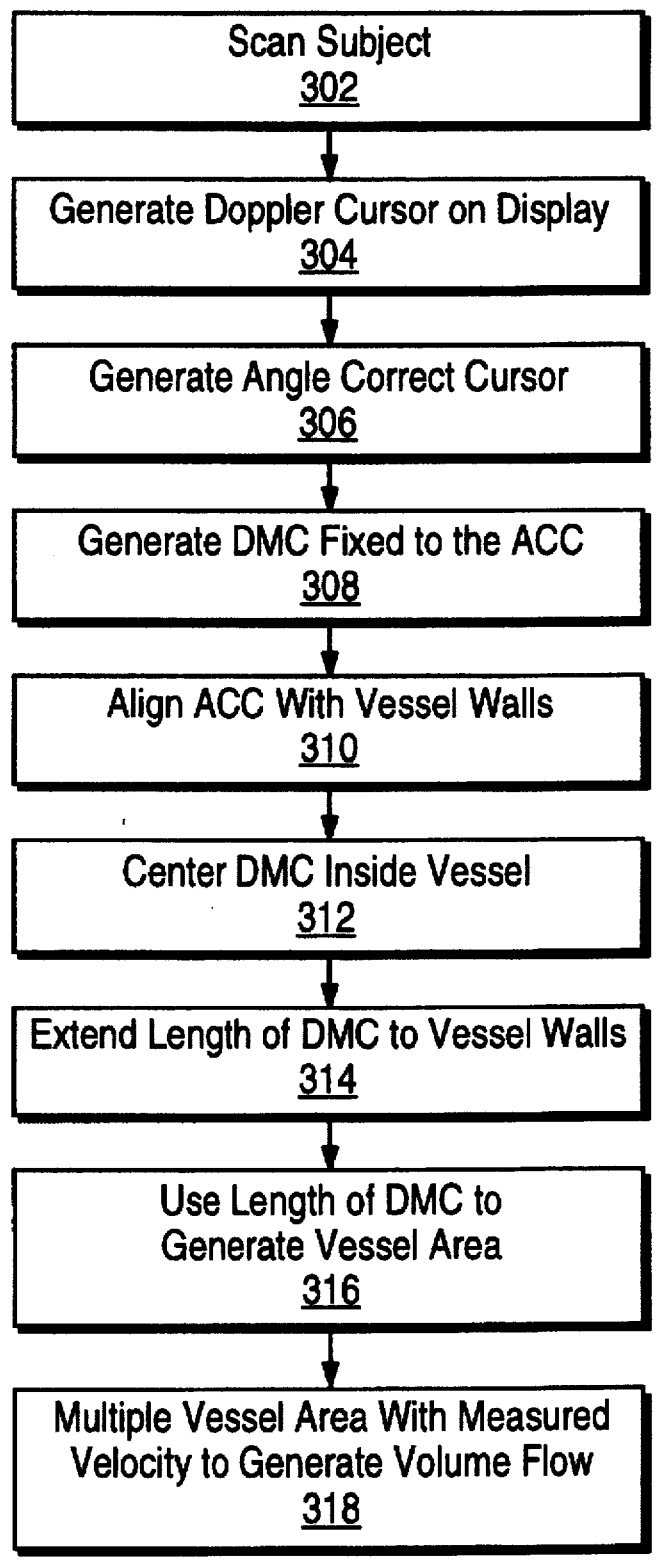

METHOD AND APPARATUS FOR GENERATING VOLUME FLOW MEASUREMENT

BACKGROUND OF THE INVENTION

1. Field of the Invention

The present invention relates to ultrasonic imaging. More specifically, the present invention relates to a method and apparatus for determining vascular measurements of a subject in an ultrasonic system.

2. Description of Related Art

An important measurement for the diagnosis and treatment of Vascular disease is the volume flow through a blood vessel. On current ultrasound systems this measurement is difficult to use and does not produce accurate and repeatable results. Current systems obtain the volume flow measurement of a subject under examination by first finding the area of the vessel in one of two ways.

The first method is to scan the vessel under study in the transverse plane. This allows an area of the vessel to be estimated using either a perimeter outlining method or by fitting an ellipse to the vessel border. The second method includes scanning the vessel sagitally and measuring the diameter to obtain the area of the vessel. After obtaining the area, a Doppler measurement is made in the vessel at approximately the same location that the area measurement was made. The Doppler spectrum is then integrated over one or more cardiac cycles to calculate the time averaged mean velocity. The volume flow of the vessel is generated by multiplying the time averaged mean velocity by the vessel area.

The prior methods of measuring volume flow, however, are difficult to perform accurately and are time consuming. Since Doppler scans can not be made transverse to the vessel it is very difficult to insure that the Doppler scan and the area measurement were done at the same location in the vessel. Measuring the diameter of the vessel in the second method eliminates this problem but it is dependent on the skill of the user to insure that the Doppler measurement coincides with the diameter measurement.

As such, what is needed is a method and apparatus for measuring a vessel area at the same location of the vessel where a Doppler measurement is taken.

SUMMARY OF THE INVENTION

A computer implemented method and apparatus for generating a vascular volume flow measurement in a living subject using an ultrasonic system by determining a velocity measurement and an area measurement at the same location in a blood vessel. The present invention generates an angle correct cursor on a display indicating where in a vessel a velocity measurement is being obtained. A diameter measure cursor is fixed perpendicular to the angle correct cursor to determine a diameter of the vessel at the same location of the vessel where the velocity measurement is obtained. The diameter is multiplied with the time averaged means velocity to accurately generate the volume flow. In one embodiment, the length of the diameter measure cursor is adjustable to extend a first end and an opposing second end of the diameter measure cursor, approximately to the walls of the vessel. In a second embodiment, the diameter measure cursor is adjustable to slide the cursor along its length to be approximately in a center of the vessel, while, maintaining the diameter measure cursor to be perpendicular to the angle correct cursor. The velocity measurement, in the present invention, is generated by emitting pulses into a subject under examination, receiving echoes and determining Doppler frequency shifts from the pulses, and translating the Doppler frequency shifts to velocity information.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3 is a flow diagram illustrating the steps performed in the present invention for generating a vascular volume flow measurement.

DETAILED DESCRIPTION OF THE INVENTION

The present invention is related to a method and apparatus for generating a volume flow measurement of a blood vessel. Although the present invention will be described with reference to certain specific embodiments such as certain specific hardware components, signals, processes, etc., in order to provide a thorough understanding of the present invention, it will be obvious, however, to one skilled in the art that these specific details may not be required to practice the instant invention. In other circumstances, well known components have not been described in detail in order to not unnecessarily obscure the present invention.

Ultrasonic System

Figure 1:
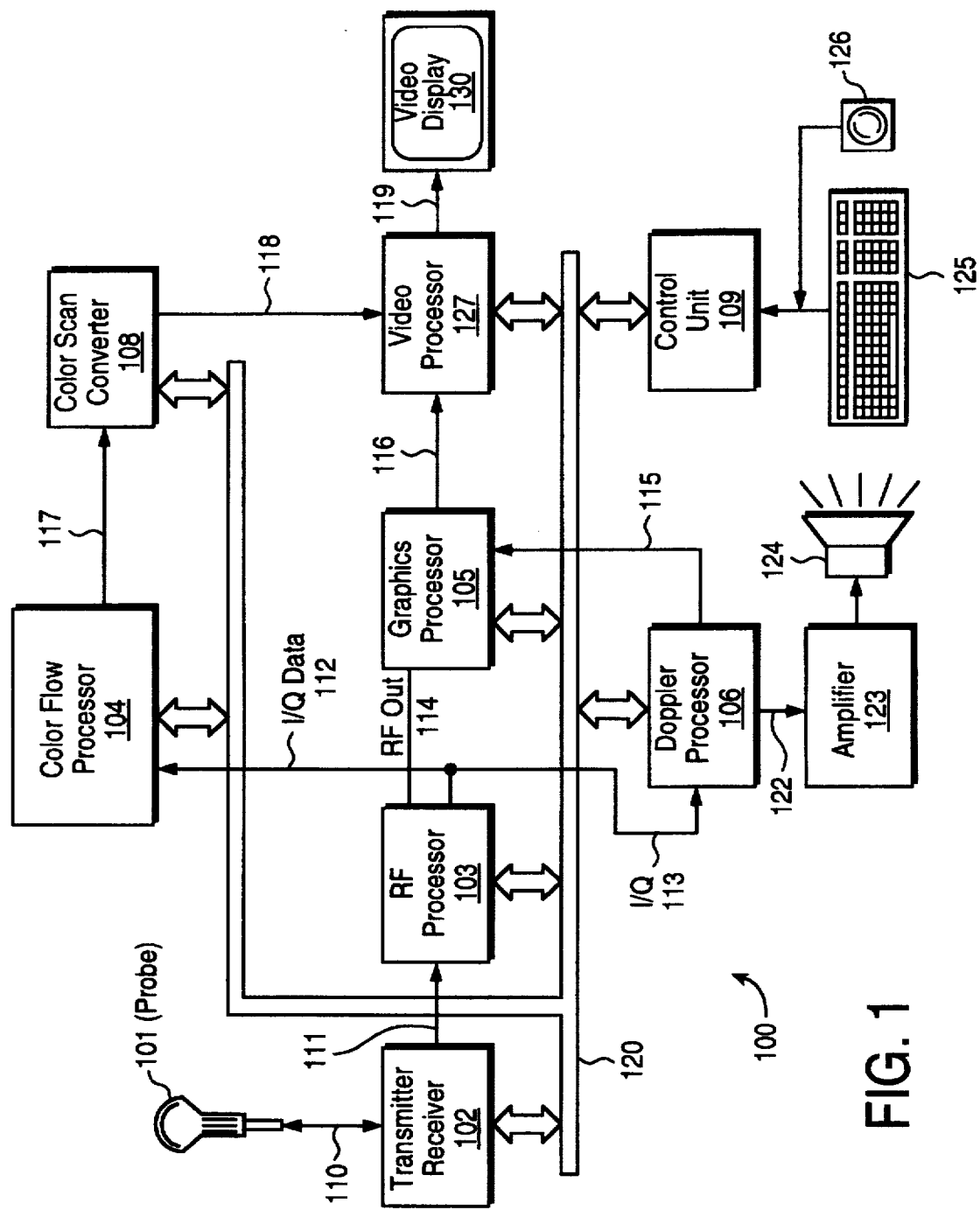
FIG. 1 is a block diagram of an ultrasonic system in which embodiments of the present invention may be implemented.

An ultrasonic system in which embodiments of the present invention may be implemented is illustrated as system 100 of FIG. 1. Imaging system 100 generally comprises a probe 101 which is coupled via line 110 to transmitter/receiver circuitry 102. Transmitter/receiver circuitry 102 is designed so that the elements in probe 101 will be fired at specified time intervals, with reflective pulses being detected using probe 101 at another given time interval. Transmitter/receiver circuitry 102 is coupled to control unit 109 via bus 120. Control unit (or host computer) 109 controls all circuitry in the imaging system via bus 120. Control unit 109 is further coupled to a keyboard 125 and a mouse, trackball or other device 126 for movement and control of information shown on video display 130 and for entering information and/or request to the control unit.

Once a pulse is received by transmitter/receiver 102, such information is transmitted by line 111 to radio frequency (RF) processor 103 for further processing. The radio frequency information (in-phase (I) and quadrature (Q) signals) is further transmitted via line 114 to a graphics processor 105 and to a Doppler processor 106 via lines 114 and 113. Information generated by the Doppler processor 106 is transmitted via line 115 to graphics processor 105. The Graphics processor 105 in return transmits scan line information to video processor 127 via line 116 for generation of black and white ultrasound information on video display 130. Such information may be transmitted in National Television Standards Committee (NTSC) format and thus be stored on video tape for later clinical examination by attending medical personnel.

In addition to information passed to graphics processor 105 and Doppler processor 106, RF processor 103 transmits I and Q signals via line 112 to color flow processor 104. Color flow processor 104 is also controlled by control unit 109 via bus 120. Color flow processor 104 is used for detecting Doppler shift and blood flow information in living tissue, and thus transmits this information via line 117 to a color scan converter 108. The color scan converter is used to interpolate point scan line information obtained from color flow processor 104, and transmit that information on line 118 to video processor 127 for representation of blood flow in the human body.

The methods of the present invention to be described may be operative either within Doppler processor 106 operating upon a raw sampled Doppler power spectrum, or it may be processed in the host computer 109 upon compressed data represented as a logorithmically compressed power spectrum.

Doppler Processor

Figure 2:
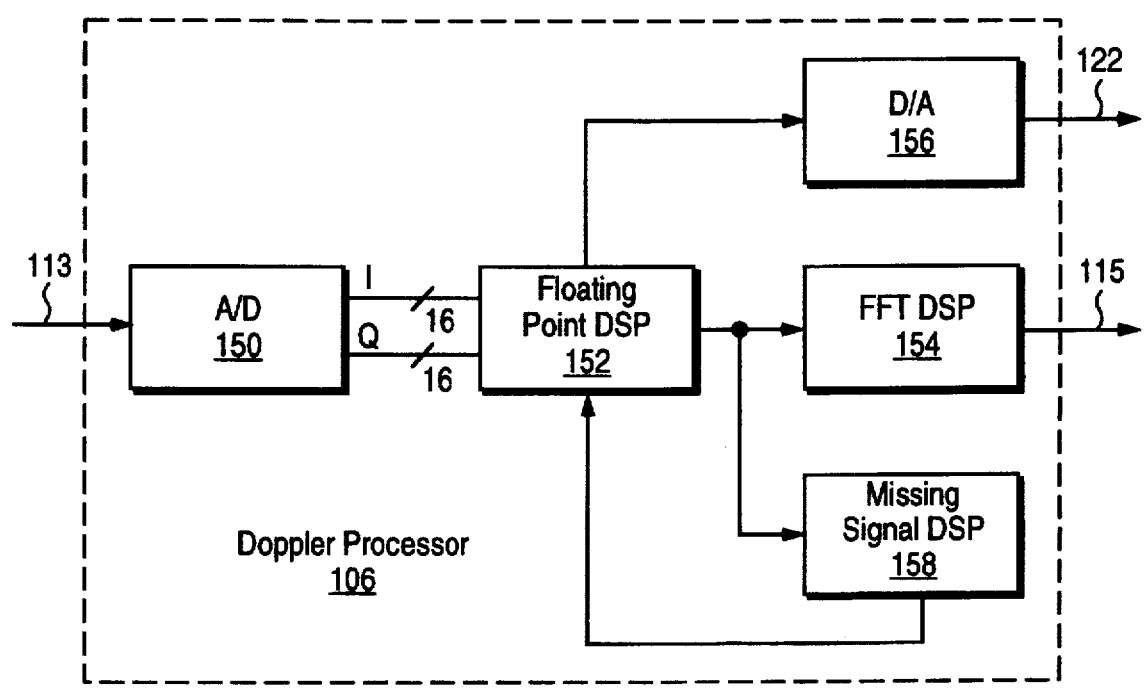
FIG. 2 is a block diagram of a Doppler processor.

The details of Doppler processor 106 are shown in more detail in FIG. 2. Doppler processor 106 receives the in-phase (I) and quadrature (Q) data generated by the RF processor 103. Doppler processor 106 includes a front end analog to digital (A/D) converter 150 which outputs the I and Q data to floating point digital signal processor (DSP) 152. Floating point DSP 152 converts the fixed point I and Q data received from A/D converter 150 to floating point, and performs a wall filter upon the data to remove any stationary artifacts. Moreover, floating point DSP 152 performs audio processing which includes forward and reverse separation of the data. This data is then output to a digital to analog (D/A) converter 156 which can be then made available to an amplifier 123 as shown in FIG. 1.

The wall filter contained within the floating point DSP 152 also outputs its data to the missing signal DSP 156. Missing signal DSP 156 includes an interpolation algorithm which is performed upon the interleaved data samples which are used to generate separate B-scan and Doppler data. Missing signal DSP 156 interpolates the missing points not provided to Doppler processor 106. Feedback is provided from missing signal DSP 156 to floating point DSP 152 in an order that the interpolated points are provided in the incoming signal path.

Floating point DSP 152 is further coupled to a Fast Fourier Transform (FFT) DSP 154 which performs a Fast Fourier Transfer on the floating point data in order to extract the requisite signal data from the input I and Q signals, in addition to other vascular processing. The output of the FFT DSP 154 provided on signal lines 115, is processed by the graphics processor 105 and retained in a display memory contained therein.

In one embodiment, each of the digital signal processors 152, 154, or 156 includes an AT&T 32C digital signal processor and any accompanying memory and control logic which is required for operation of the predetermined functions. Thus, although each of the DSP's include a small memory area for computational purposes, the algorithms performed within each of the DSP's may be loaded from a long term memory (e.g. a hard disk drive or read-only memory (ROM), or other non-volatile storage means) into the volatile memory.

In either the host computer 109 or Doppler processor 106, the methods of the present invention can be implemented in a computer programming language such as a high-level (e.g., C or C++) or assembly programming language, converted to machine code, and loaded from long-term storage at system run-time for execution. Alternatively, the present invention may be implemented in discrete hardware components such as large-scale integrated circuits (LSI's), application-specific integrated circuits (ASIC's) or in firmware such as electrically erasable programmable read-only memory (EEPROM's).

Volume Flow Measurement

As illustrated in the flow diagram FIG. 3, volume flow measurement starts at block 302, an operator sagittally scans a subject under examination using a duplex scanner which includes a simultaneous B-scan and Doppler scanner. The B-scan generates a cross-sectional real-time image of the subject's vessel. In a second embodiment, the operator may scan with a triplex scanner, which includes simultaneous B-scan, color, and Doppler scanning.

Figure 4A:
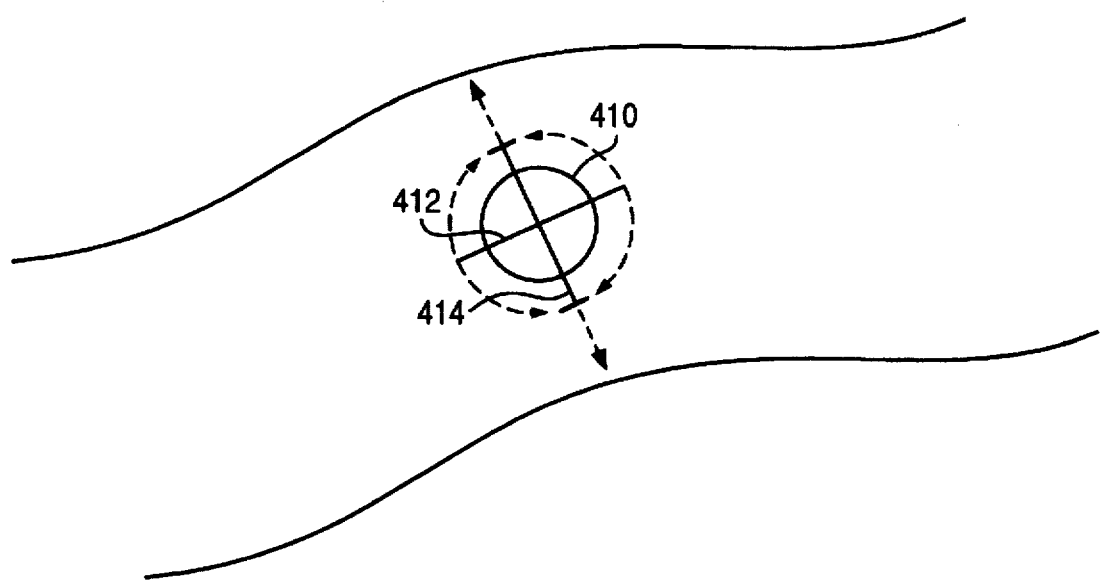
FIGS. 4a and 4b are illustrations of the diameter measure cursor of the present invention displayed on a cross-section of a vessel of a subject under examination.

In block 304, a Doppler cursor 410 is generated on the video display showing a volume of the vessel where the Doppler measurement is generated, as illustrated in FIG. 4a. In block 306, an angle correct cursor (ACC) 412 is generated, also at the same location of the vessel where the Doppler measurement generated. The ACC, also illustrated in FIG. 4a, is used by the operator to signify the direction of the blood flow in the vessel under examination. In one embodiment, the ACC is rotated on its axis to align the ACC with the walls of the vessel at the point where the Doppler measurement is generated. This is done under operator control. The ACC is typically provided when generating a Doppler measurement to provide a means for correcting the Doppler shift so that an accurate velocity of the blood flow may be measured.

The present invention, at block 308, generates a diameter measure cursor (DMC) 414 fixed perpendicular to the ACC. The DMC provides the novel advantage of generating the diameter of the vessel at the same location where the Doppler measurement is generated to accurately generate a volume flow measurement. In one embodiment, the DMC is provided in a shape of a capital letter 'I', and is maintained in a 90° . relationship to the angle correct cursor. In alternative embodiment, any shape having a length and edges could be used as the DMC.

In blocks 310–316, the DMC is adjusted to measure the diameter of the vessel. In block 310, an operator rotates the ACC to be aligned with the walls of the vessel as described. In one embodiment, one value jointly representing the angle position of the diameter measurement and angle correct cursor is stored in a register of the video processor 127. An interrupt is generated by the control unit 109 in response to an operator inputting a request to rotate either the DMC or the ACC. In response to the interrupt, the video processor determines the subject of the request and corrects the value jointly representing the angle position of the DMC and the ACC. In alternative embodiments, two separate values representing the DMC and ACC, respectively, may be provided. More over, in other embodiments, values representing the angle position, as well other values representing remaining physical features of the ACC and DMC, may be stored in registers of other DSP's of the imaging system 100 or processors of the control unit 109, as well as any memory device provided therein.

Figure 4B:
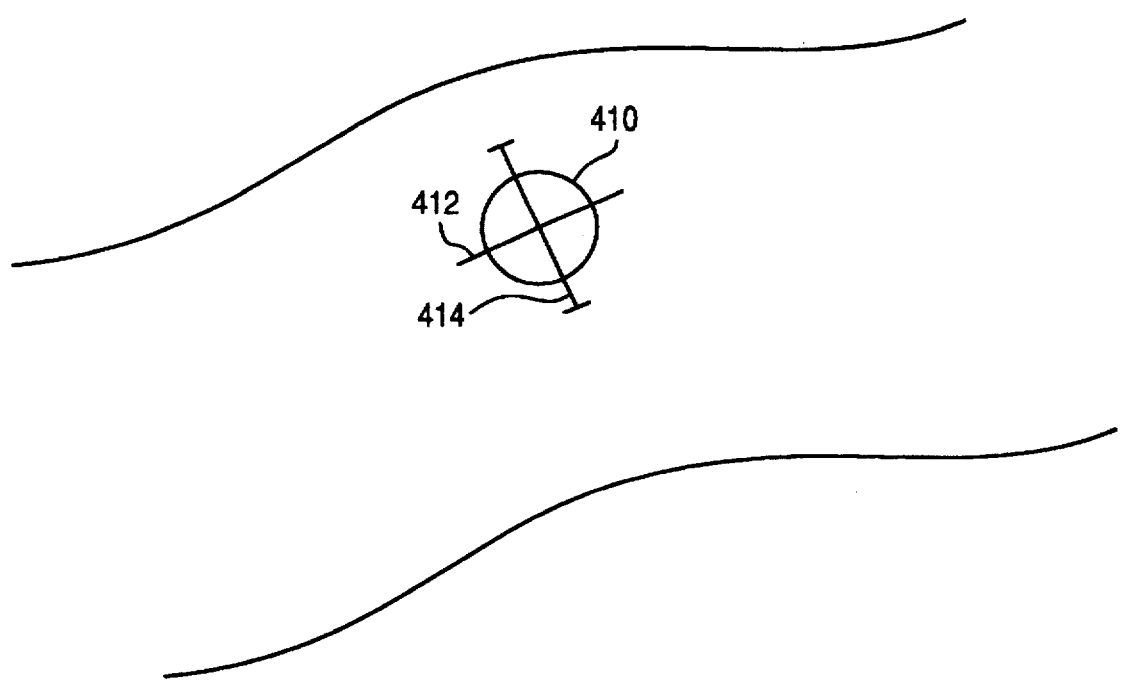

In block 312, the position of the DMC is adjusted by sliding the DMC along its length to center the DMC inside the vessel walls. The position of the DMC is typically adjusted when the ACC is not in the middle of the blood vessel, as illustrated in FIG. 4b. When adjusted, the DMC is constrained to maintain a right angle relationship with the ACC. In one embodiment, a value representing the position of the DMC as shown on the video display 130, is stored in a register of the video processor. An interrupt is generated by the control unit 109 in response to an operator inputting a request to adjust the position of the DMC. In response to the interrupt, the video processor determines the subject of the request and corrects the value representing the position of the DMC.

In block 314, the length of the diameter measurement cursor is adjusted to place the edges of the cursor adjacent to the walls of the blood vessel. In one embodiment, the length of the DMC is adjusted by equally extending or retracting the arms of the DMC. In one embodiment, a value representing the length of the DMC as shown on the video display 130 is stored in a register of the video processor. An interrupt is generated by the control unit 109 in response to an operator inputting a request to increase or decrease the length of the diameter measurement cursor. In response to the interrupt, the video processor determines the subject of the request and corrects the value representing the length of the diameter measurement cursor.

In block 316, the area of the vessel is generated using the length of the DMC as the diameter (D) in the equation (Area=($\frac{1}{4}$)$\pi D^2$). In the final block 318, the volume flow measurement for the volume of the vessel being sampled is obtained by multiplying the area of the vessel with the time average velocity means generated by the Doppler measurement.

What is claimed is:

1. A method for generating a vascular volume flow measurement in a living subject using an ultrasonic system, the method comprising the steps of:
   a) generating a velocity measurement of a volume in a vessel;
   b) generating a rotatable angle correct cursor on a display, the angle correct cursor indicating a point of the vessel where the velocity measurement is generated, said angle correct cursor operable to determine an angle of said vessel for correcting said velocity measurement; and
   c) generating a diameter measure cursor on the display, the diameter measure cursor is fixed to the angle correct cursor and is used to determine an approximate diameter of the vessel at the point of the vessel where the velocity measurement is generated.

2. The method of claim 1, wherein the velocity measurement is generated by emitting pulses into a subject under examination, receiving echoes and determining Doppler frequency shifts from the pulses, and translating the Doppler frequency shifts to velocity information.

3. The method of claim 2, wherein the diameter measure cursor is perpendicular to the angle correct cursor.

4. A method for generating a vascular volume flow measurement in a living subject using an ultrasonic system, the method comprising the steps of:
   a) generating a velocity measurement of a volume in a vessel;
   b) generating an angle correct cursor on a display, the angle correct cursor indicating a point of the vessel where the velocity measurement is generated; and
   c) generating a diameter measure cursor on the display, the diameter measure cursor is fixed to the angle correct cursor and is used to determine an approximate diameter of the vessel at the point of the vessel where the velocity measurement is generated, wherein the diameter measure cursor and the angle correct cursor are jointly rotatable.

5. The method of claim 4, further includes the step of:
   d) adjusting a length of the diameter measure cursor.

6. The method of claim 5, wherein the step of adjusting the length of the diameter measure cursor includes extending a first end and an opposing second end of the diameter measure cursor, approximately, to the edges of the vessel.

7. The method of claim 5, further including the step of:
   e) adjusting a position of the diameter measure cursor.

8. The method of claim 7, wherein the step of adjusting a position of the diameter measure cursor includes sliding the diameter measure cursor along the length of the diameter measure cursor to be approximately in a center of the vessel and maintaining the diameter measure cursor to be perpendicular to the angle correct cursor.

9. The method of claim 8, wherein the diameter measure cursor is a shape of a capital letter I.

10. An apparatus for making vascular volume flow measurements within a living subject in an ultrasonic system comprising:
    a first circuit for determining a velocity in a vessel by emitting pulses into the subject under examination, receiving echoes in response to the pulses and determining Doppler frequency shifts from the pulses, and translating the Doppler frequency shifts to velocity information;
    a second circuit coupled to the first circuit for generating a rotatable angle correct cursor on a display of the system, the angle correct cursor showing an area of the vessel where the velocity is determined, said angle correct cursor operable to determine an angle of said vessel for correcting said velocity; and
    a third circuit coupled to the second circuit for generating a diameter measuring cursor on the display for determining a diameter of the area of the vessel where the velocity is determined, wherein the diameter measuring cursor is fixed to the angle correct cursor.

11. The apparatus of claim 10, further comprising a fourth circuit coupled to the third circuit for using the diameter generated by the third circuit and the velocity generated by the first circuit to generate a measurement of a volume flow at the area of the vessel where the velocity measurement is determined.

12. The apparatus of claim 11, wherein the diameter measure cursor generated by the third circuit is perpendicular to the angle correct cursor.

13. An apparatus for making vascular volume flow measurements within a living subject in an ultrasonic system comprising:
    a first circuit for determining a velocity in a vessel by emitting pulses into the subject under examination, receiving echoes in response to the pulses and determining Doppler frequency shifts from the pulses, and translating the Doppler frequency shifts to velocity information;
    a second circuit coupled to the first circuit for generating an angle correct cursor on a display of the system, the angle correct cursor showing an area of the vessel where the velocity is determined; and
    a third circuit coupled to the second circuit for generating a diameter measuring cursor on the display for determining a diameter of the area of the vessel where the velocity is determined, wherein the diameter measuring cursor is fixed to the angle correct cursor, wherein the diameter measure cursor generated by the third circuit and the angle correct cursor generated by the second circuit, are jointly rotatable.

14. The apparatus of claim 13, wherein the third circuit includes the ability to adjust a length of the diameter measure cursor.

15. The apparatus of claim 14, wherein the third circuit further includes the ability to extend a first arm and an opposing second arm of the diameter measure cursor.

16. The apparatus of claim 15, wherein the third circuit further includes the ability to slide the diameter measure cursor along a length of the diameter measure cursor and maintain the diameter measure cursor to be perpendicular to the angle correct cursor.

17. The apparatus of claim 15, wherein the diameter measure cursor generated by the third circuit is a shape of a capital letter I.

18. An apparatus for making vascular volume flow measurements within a living subject in an ultrasonic system comprising:

a velocity determining means for determining a velocity in a vessel by emitting pulses into the subject under examination, receiving echoes in response to the pulses and determining Doppler frequency shifts from the pulses, and translating the Doppler frequency shifts to velocity information;

a rotatable angle correct cursor generating means coupled to the velocity determining means for generating an angle correct cursor on a display of the system, the angle correct cursor showing an area of the vessel where the velocity is determined, said angle correct cursor operable to determine an angle of said vessel for correcting said velocity; and a diameter measuring cursor means coupled to the angle correct cursor generating means for generating a diameter measuring cursor on the display for determining a diameter of the area of the vessel where the velocity is determined, wherein the diameter measuring cursor is fixed to the angle correct cursor.

19. The apparatus of claim 18, further comprises a volume flow measurement means for generating a volume flow measurement at the area of the vessel where the velocity measurement is determined.

20. The apparatus of claim 19, wherein the diameter measure cursor is approximately perpendicular to the angle correct cursor.

21. An apparatus for making vascular volume flow measurements within a living subject in an ultrasonic system comprising:

a velocity determining means for determining a velocity in a vessel by emitting pulses into the subject under examination, receiving echoes in response to the pulses and determining Doppler frequency shifts from the pulses, and translating the Doppler frequency shifts to velocity information;

an angle correct cursor generating means coupled to the velocity determining means for generating an angle correct cursor on a display of the system, the angle correct cursor showing an area of the vessel where the velocity is determined; and a diameter measuring cursor means coupled to the angle correct cursor generating means for generating a diameter measuring cursor on the display for determining a diameter of the area of the vessel where the velocity is determined, wherein the diameter measuring cursor is fixed to the angle correct cursor, further comprises a rotation means coupled to the volume flow measurement means for jointly rotating the diameter measure cursor and the angle correct cursor.

22. The apparatus of claim 21, further comprises a length adjusting means coupled to the volume flow measurement means for adjusting a length of the diameter measure cursor.

23. The apparatus of claim 22, the means for adjusting the length of the diameter measure cursor includes a first circuit for extending a first arm and an opposing second arm of the diameter measure cursor.

24. The apparatus of claim 23, a sliding means coupled to the means for adjusting the length of the diameter measure cursor for sliding the diameter measure cursor along a length of the diameter measure cursor and maintaining the diameter measure cursor to be approximately perpendicular to the angle correct cursor.

25. The apparatus of claim 24, wherein the diameter measure cursor is a shape of a capital letter I.

* * * * *